(12) United States Patent
Imai

(10) Patent No.: US 11,134,920 B2
(45) Date of Patent: Oct. 5, 2021

(54) ULTRASOUND DIAGNOSTIC APPARATUS AND METHOD FOR DETERMINATION OF AN IMAGING PART

(71) Applicant: FUJIFILM Corporation, Tokyo (JP)

(72) Inventor: Yoshiro Imai, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 448 days.

(21) Appl. No.: 16/059,234

(22) Filed: Aug. 9, 2018

(65) Prior Publication Data

US 2018/0344289 A1 Dec. 6, 2018

Related U.S. Application Data

(63) Continuation of application No. PCT/JP2017/000591, filed on Jan. 11, 2017.

(30) Foreign Application Priority Data

Feb. 25, 2016 (JP) .............................. JP2016-034610

(51) Int. Cl.
*A61B 8/00* (2006.01)
*A61B 8/14* (2006.01)
*A61B 8/08* (2006.01)

(52) U.S. Cl.
CPC .............. *A61B 8/461* (2013.01); *A61B 8/085* (2013.01); *A61B 8/14* (2013.01); *A61B 8/4444* (2013.01);
(Continued)

(58) Field of Classification Search
CPC ....... A61B 8/461; A61B 8/085; A61B 8/5223; A61B 8/467; A61B 8/585; A61B 8/54;
(Continued)

(56) References Cited

U.S. PATENT DOCUMENTS

2005/0054927 A1 3/2005 Love
2012/0203106 A1 8/2012 Matsunaga et al.
(Continued)

FOREIGN PATENT DOCUMENTS

CN 103919572 A 7/2014
JP 4-224738 A 8/1992
(Continued)

OTHER PUBLICATIONS

Chinese Office Action and Search Report for corresponding Chinese Application No. 201780013338.2, dated Aug. 25, 2020, with English translation of the Office Action.
(Continued)

*Primary Examiner* — Serkan Akar
*Assistant Examiner* — Renee C Langhals
(74) *Attorney, Agent, or Firm* — Birch, Stewart, Kolasch & Birch, LLP

(57) ABSTRACT

An ultrasound diagnostic apparatus includes: a collation pattern memory that stores a plurality of collation patterns corresponding to a plurality of examination parts of a subject in advance; an information input unit that is used by a user to input examination type information; a determination order decision unit that decides a determination order of the plurality of examination parts to be continuously examined, on the basis of the examination type information input to the information input unit; and a part determination unit that reads the collation patterns corresponding to the examination parts to be continuously examined from the collation pattern memory according to the determination order decided by the determination order decision unit and sequentially collates the ultrasound image in the determination order using the read collation patterns to determine an imaging part of the subject.

7 Claims, 5 Drawing Sheets

(52) U.S. Cl.
CPC ............... *A61B 8/467* (2013.01); *A61B 8/52* (2013.01); *A61B 8/5223* (2013.01); *A61B 8/54* (2013.01); *A61B 8/585* (2013.01); *G06T 2207/10132* (2013.01)

(58) Field of Classification Search
CPC ........... A61B 8/14; A61B 8/4444; A61B 8/52; G06T 2207/10132; G16H 50/30
USPC ........................................................ 600/437
See application file for complete search history.

(56) References Cited

U.S. PATENT DOCUMENTS

| | | |
|---|---|---|
| 2013/0109970 A1 | 5/2013 | Higuchi et al. |
| 2014/0088427 A1 | 3/2014 | Tashiro |
| 2014/0200451 A1 | 7/2014 | Hayashi et al. |
| 2014/0309530 A1 | 10/2014 | Chong |

FOREIGN PATENT DOCUMENTS

| | | | |
|---|---|---|---|
| JP | 2943015 B2 | * | 8/1999 |
| JP | 2013-111309 A | | 6/2013 |
| JP | 2013111309 A | * | 6/2013 |
| JP | 2016-2405 A | | 1/2016 |
| WO | WO 2012/161040 A1 | | 11/2012 |
| WO | WO 2013/039192 A1 | | 3/2013 |

OTHER PUBLICATIONS

International Preliminary Report on Patentability and Written Opinion of the International Searching Authority (forms PCT/IB/373, PCT/ISA/237 and PCT/IB/326), dated Sep. 7, 2018, for corresponding International Application No. PCT/JP2017/000591, with an English translation of the WO.

International Search Report (form PCT/ISA/210), dated Mar. 14, 2017, for corresponding International Application No. PCT/JP2017/000591, with an English translation.

Extended European Search Report dated Dec. 12, 2018, for corresponding European Application No. 17755982.0.

* cited by examiner

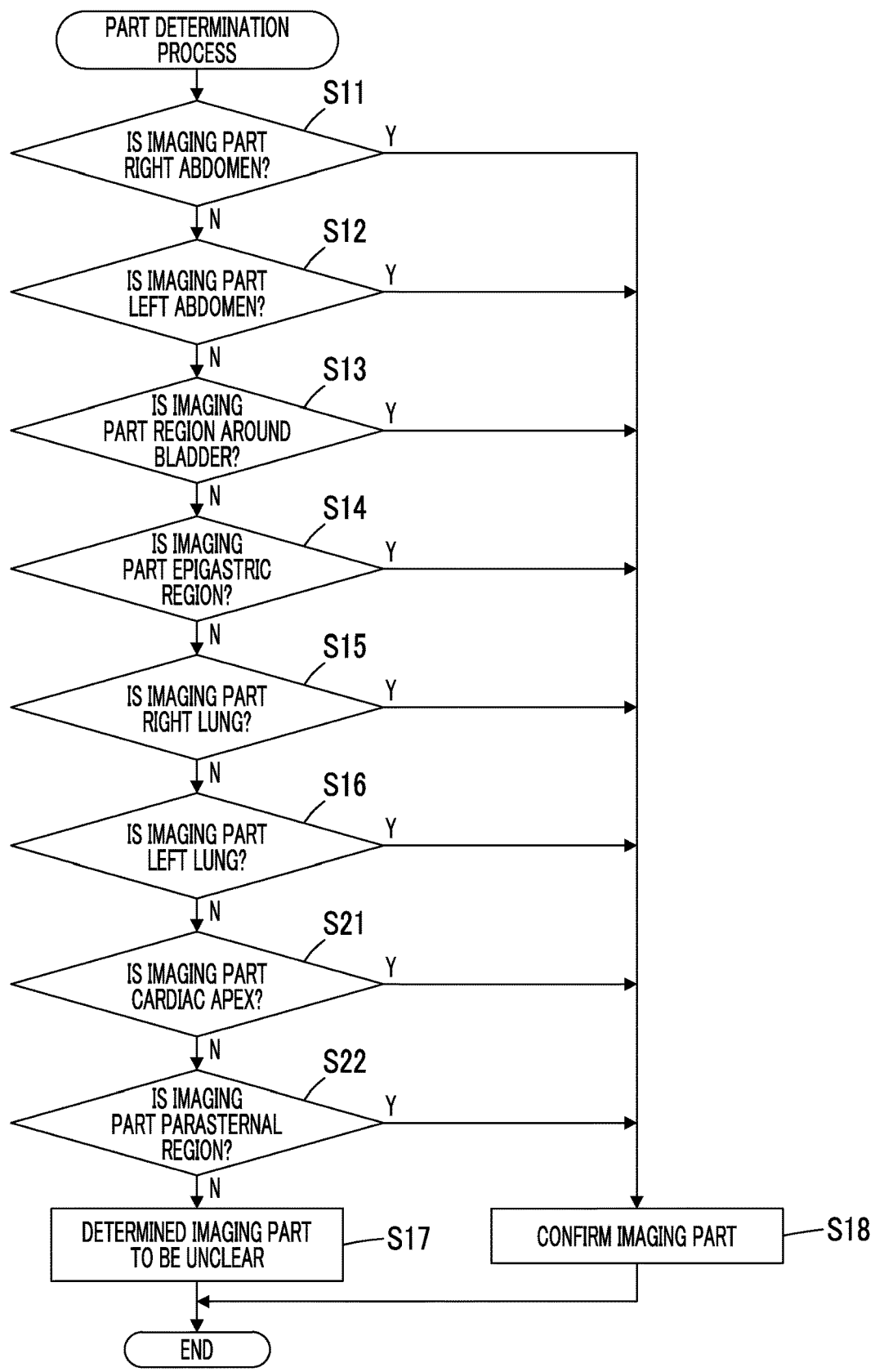

ULTRASOUND DIAGNOSTIC APPARATUS AND METHOD FOR DETERMINATION OF AN IMAGING PART

CROSS-REFERENCE TO RELATED APPLICATIONS

This application is a Continuation of PCT International Application No. PCT/JP2017/000591 filed on Jan. 11, 2017, which claims priority under 35 U.S.C. § 119(a) to Japanese Patent Application No. 2016-034610 filed on Feb. 25, 2016. The above application is hereby expressly incorporated by reference, in its entirety, into the present application.

BACKGROUND OF THE INVENTION

1. Field of the Invention

The present invention relates to an ultrasound diagnostic apparatus and a method for controlling the ultrasound diagnostic apparatus, and more particularly, to an ultrasound diagnostic apparatus that determines an imaging part of a subject on the basis of an ultrasound image.

2. Description of the Related Art

In the related art, an ultrasound diagnostic apparatus using an ultrasound image has been put to practical use in the medical field. In general, in this type of ultrasound diagnostic apparatus, an ultrasound probe provided with an array transducer scans a subject with an ultrasound beam and receives ultrasound echoes from the subject and the received signal is electrically processed to generate an ultrasound image.

In a case in which the ultrasound diagnostic apparatus is used to diagnose the subject, the user sets imaging conditions according to an imaging part in order to obtain ultrasound images suitable for diagnosis for each examination part. However, in a case in which a plurality of examination parts of the subject are continuously examined, the user needs to reset the imaging conditions according to the examination part whenever the examination part is changed. As a result, there is a concern that it will take a long time for diagnosis. For this reason, JP1992-224738A (JP-H04-224738A) discloses an ultrasound diagnostic apparatus which determines an imaging part from a generated ultrasound image, using collation patterns corresponding to each examination part that is stored in advance, and sets a scanning parameter suitable for the imaging part on the basis of the determination result.

SUMMARY OF THE INVENTION

However, for example, in a case in which an extended focused assessment with sonography for trauma (eFAST) examination that continuously examines a plurality of examination parts is performed, the number of examination part candidates increases. As such, in a case in which the number of examination part candidates increases, the number of collation patterns used by the ultrasound diagnostic apparatus disclosed in JP1992-224738A (JP-H04-224738A) to determine the imaging part increases in order to respond to these examination part candidates. As a result, there is a concern that it will take a long time until the determination of the imaging part is completed. In addition, in a case in which the ultrasound image of an examination part other than the examination parts corresponding to the collation patterns which have been stored in advance is obtained, it is difficult to determine the imaging part and a part determination process is continuously performed until all of the collation patterns are used. Therefore, there is a concern that it will take a long time unit the process proceeds to an operation subsequent to the part determination process. As a result, there is a concern that the setting of the scanning parameter suitable for the imaging part will be delayed, which hinders diagnosis.

The invention has been made in order to solve the problems of the related art and an object of the invention is to provide an ultrasound diagnostic apparatus and a method for controlling the ultrasound diagnostic apparatus that can prevent the time required to determine an imaging part in an ultrasound image from increasing even in a case in which the number of examination part candidates increases.

An ultrasound diagnostic apparatus according to the invention comprises: an ultrasound probe; an imaging unit that transmits and receives an ultrasound beam to and from a subject using the ultrasound probe and converts a received signal output from the ultrasound probe into an image to generate an ultrasound image of the subject; a collation pattern memory that stores a plurality of collation patterns corresponding to a plurality of examination parts of the subject in advance; an information input unit that is used by a user to input examination type information indicating content of an examination for continuously examining the plurality of examination parts; a determination order decision unit that decides a determination order of the plurality of examination parts to be continuously examined, on the basis of the examination type information input to the information input unit; and a part determination unit that reads the collation patterns corresponding to the examination parts to be continuously examined from the collation pattern memory according to the determination order decided by the determination order decision unit and sequentially collates the ultrasound image generated by the imaging unit in the determination order using the read collation patterns to determine an imaging part of the subject.

The part determination unit may read a collation pattern corresponding to an examination part which is located in the vicinity of the examination part corresponding to the read collation pattern from the collation pattern memory, in addition to the collation patterns read from the collation pattern memory according to the determination order, and determine the imaging part.

The determination order decision unit may store content of a plurality of continuous examinations for continuously examining the plurality of examination parts in advance. In a case in which the user inputs a continuous examination selected from the plurality of continuous examinations as the examination type information to the information input unit, the determination order decision unit may decide the determination order of the plurality of examination parts corresponding to the input continuous examination.

The examination type information may be input as a list of the plurality of examination parts to be continuously examined to the information input unit by the user. The determination order decision unit may decide the determination order of the plurality of examination parts on the basis of the list input from the information input unit.

The ultrasound diagnostic apparatus may further comprise an imaging condition setting unit that sets imaging conditions corresponding to the imaging part determined by the part determination unit. The imaging unit may generate the ultrasound image according to the imaging conditions set by the imaging condition setting unit.

A method for controlling an ultrasound diagnostic apparatus according to the invention comprises: a step of transmitting and receiving an ultrasound beam to and from a subject using an ultrasound probe and converting a received signal output from the ultrasound probe into an image to generate an ultrasound image of the subject; a step of allowing a user to input examination type information indicating content of an examination for continuously examining a plurality of examination parts; a step of deciding a determination order of the plurality of examination parts to be continuously examined, on the basis of the input examination type information; and a step of reading collation patterns corresponding to the examination parts to be continuously examined from a plurality of collation patterns, which correspond to the plurality of examination parts and are stored in advance, according to the decided determination order and sequentially collating the ultrasound image in the determination order using the read collation patterns to determine an imaging part of the subject.

According to the invention, an ultrasound beam is transmitted and received to and from the subject by the ultrasound probe and the received signal output from the ultrasound probe is converted into an image to generate an ultrasound image of the subject. In a case in which the user inputs the examination type information indicating the content of the examination for continuously examining a plurality of examination parts, the determination order of the plurality of examination parts to be continuously examined is decided on the basis of the input examination type information. Collation patterns corresponding to the examination parts to be continuously examined are read from a plurality of collation patterns, which correspond to the plurality of examination parts and are stored in advance, according to the decided determination order and the ultrasound image is sequentially collated in the determination order using the read collation patterns to determine the imaging part of the subject. Therefore, it is possible to prevent the time required to determine the imaging part in the ultrasound image from increasing even in a case in which the number of examination part candidates increases.

BRIEF DESCRIPTION OF THE DRAWINGS

FIG. 6 is a flowchart illustrating a part determination process according to Embodiment 2.

DESCRIPTION OF THE PREFERRED EMBODIMENTS

Hereinafter, embodiments of the invention will be described with reference to the accompanying drawings.

Embodiment 1

Figure 1:
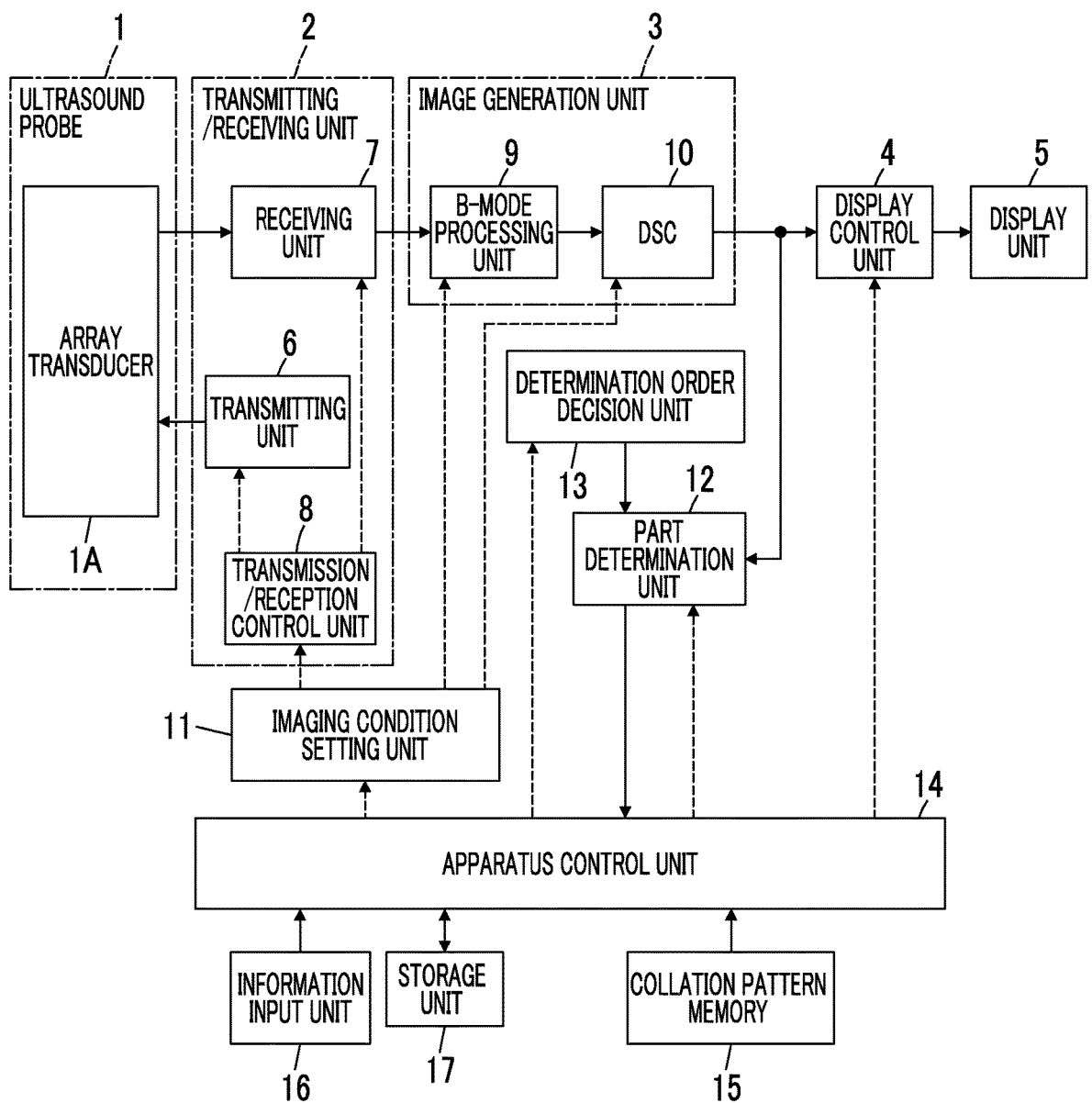
FIG. 1 is a block diagram illustrating the configuration of an ultrasound diagnostic apparatus according to Embodiment 1 of the invention.

FIG. 1 illustrates the configuration of an ultrasound diagnostic apparatus according to Embodiment 1 of the invention. The ultrasound diagnostic apparatus includes an ultrasound probe 1 provided with an array transducer 1A. An image generation unit 3 is connected to the ultrasound probe 1 through a transmitting/receiving unit 2 and a display unit 5 is connected to the image generation unit 3 through a display control unit 4.

The transmitting/receiving unit 2 includes a transmitting unit 6 and a receiving unit 7 that are connected to the array transducer 1A of the ultrasound probe 1 and a transmission/reception control unit 8 that is connected to the transmitting unit 6 and the receiving unit 7. The image generation unit 3 includes a brightness-mode (B-mode) processing unit 9 that is connected to the receiving unit 7 of the transmitting/receiving unit 2 and a digital scan converter (DSC) 10 that is connected to the B-mode processing unit 9. The display control unit 4 is connected to the DSC 10. An imaging condition setting unit 11 is connected to the transmission/reception control unit 8 of the transmitting/receiving unit 2 and the B-mode processing unit 9 and the DSC 10 of the image generation unit 3.

In addition, a part determination unit 12 is connected to the DSC 10 and a determination order decision unit 13 is connected to of the part determination unit 12.

An apparatus control unit 14 is connected to the imaging condition setting unit 11, the part determination unit 12, the determination order decision unit 13, and the display control unit 4. In addition, a collation pattern memory 15, an information input unit 16, and a storage unit 17 are connected to the apparatus control unit 14.

The array transducer 1A of the ultrasound probe 1 includes a plurality of ultrasound transducers that are one-dimensionally or two-dimensionally arranged. Each of the ultrasound transducers transmits ultrasonic waves in response to a driving signal supplied from the transmitting unit 6. In addition, each of the ultrasound transducers receives ultrasound echoes from a subject and outputs a received signal. Each ultrasound transducer is, for example, a transducer in which electrodes are formed at both ends of a piezoelectric body made of piezoelectric ceramic typified by lead zirconate titanate (PZT), a polymer piezoelectric element typified by polyvinylidene difluoride (PVDF), or a piezoelectric crystal typified by lead magnesium niobate-lead titanate (PMN-PT).

In a case in which a pulsed voltage or a continuous-wave voltage is applied to the electrodes of the transducer, the piezoelectric body is expanded and contracted and pulsed or continuous ultrasonic waves are generated from each transducer. The ultrasonic waves are combined to form an ultrasound beam. In addition, each transducer receives propagated ultrasonic waves, is expanded and contracted, and generates an electric signal. The electric signal is output as a received ultrasound signal.

The transmitting/receiving unit 2 transmits and receives an ultrasound beam according to the set ultrasound beam scanning conditions and the image generation unit 3 generates a B-mode image signal according to the set ultrasound image generation conditions. Therefore, the transmitting/receiving unit 2 and the image generation unit 3 form an imaging unit. In addition, imaging conditions for the imaging unit are formed by ultrasound beam scanning conditions for the transmitting/receiving unit 2 and ultrasound image generation conditions for the image generation unit 3.

The transmitting unit 6 of the transmitting/receiving unit 2 includes, for example, a plurality of pulse generators, adjusts the amount of delay of each driving signal such that the ultrasonic waves transmitted from a plurality of ultrasound transducers in the array transducer 1A form an ultrasound beam, on the basis of a transmission delay pattern selected according to a control signal from the transmission/reception control unit 8, and supplies the driving signals to the plurality of ultrasound transducers.

Figure 2:
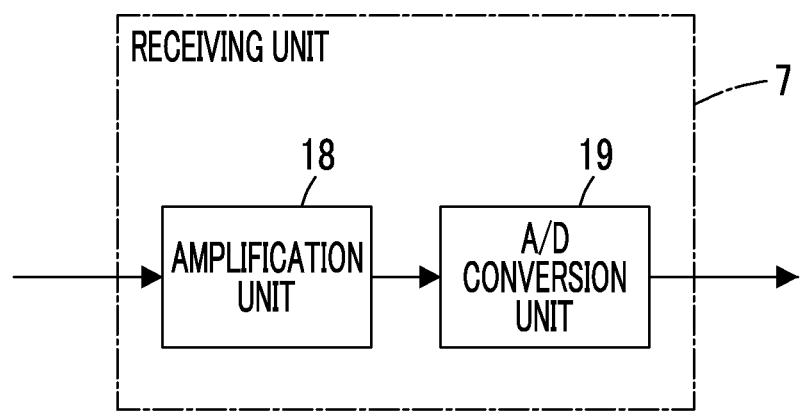
FIG. 2 is a block diagram illustrating the internal configuration of a receiving unit.

As illustrated in FIG. 2, the receiving unit 7 has a configuration in which an amplification unit 18 and an analog/digital (A/D) conversion unit 19 are sequentially connected in series. The receiving unit 7 amplifies the received signals transmitted from each ultrasound transducer of the array transducer 1A with the amplification unit 18 and performs A/D conversion for the received signals with the A/D conversion unit 19 to generate digital received data.

The transmission/reception control unit 8 controls the transmitting unit 6 and the receiving unit 7 on the basis of various control signals transmitted from the apparatus control unit 14 such that the transmission of an ultrasound pulse to a subject and the reception of an ultrasound echo from the subject are repeated at a pulse repetition frequency (PRF) interval.

Figure 3:
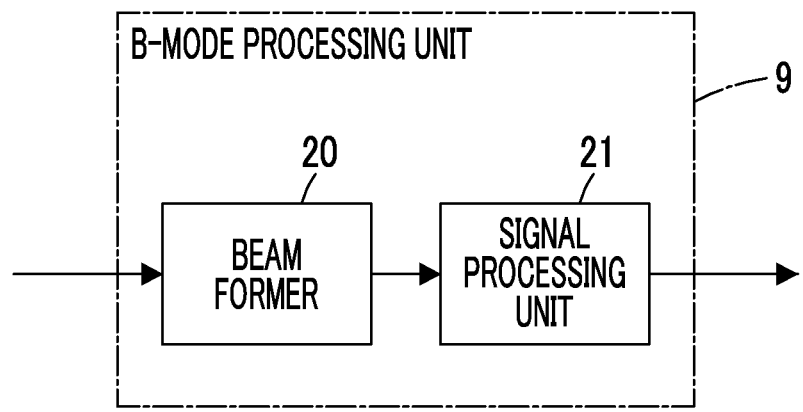
FIG. 3 is a block diagram illustrating the internal configuration of a B-mode processing unit.

The B-mode processing unit 9 of the image generation unit 3 has a configuration in which a beam former 20 and a signal processing unit 21 are sequentially connected in series, as illustrated in FIG. 3. The beam former 20 applies a delay to each received data item output from the receiving unit 7 of the transmitting/receiving unit 2 according to a sound speed or a sound speed distribution set on the basis of a reception delay pattern selected according to a control signal from the imaging condition setting unit 11 and adds the received data to perform a reception focusing process. A sound ray signal in which the focus of an ultrasound echo subjected to phasing addition is narrowed is generated by the reception focusing process.

The signal processing unit 21 corrects the attenuation of the sound ray signal generated by the beam former 20 depending on a distance according to the depth of the reflection position of ultrasonic waves and then performs an envelope detection process. In addition, the signal processing unit 21 performs various types of necessary image processing including a gradation process to generate a B-mode image signal which is tomographic image information related to the tissues of the subject.

The DSC 10 of the image generation unit 3 converts the B-mode image signal generated by the signal processing unit 21 into an image signal based on a general television signal scanning system (raster conversion).

The display control unit 4 displays a B-mode image on the display unit 5 on the basis of the B-mode image signal generated by the image generation unit 3.

The display unit 5 includes a display device, such as a liquid crystal display (LCD), and displays the B-mode image under the control of the display control unit 4.

A plurality of collation patterns corresponding to a plurality of examination parts of the subject are stored in the collation pattern memory 15 in advance.

The information input unit 16 is used by a user to perform an input operation and may include, for example, a keyboard, a mouse, a trackball, and a touch panel.

Here, for example, an operation of continuously examining a plurality of examination parts, such as an eFAST examination, an abdomen routine examination, or a circulatory organ routine examination, is defined as a continuous examination. A continuous examination that is selected from a plurality of continuous examination candidates by the user is input as examination type information to the information input unit 16.

The determination order decision unit 13 decides a plurality of examination parts to be continuously examined on the basis of the examination type information input to the information input unit 16 and decides a determination order in which the examination parts are determined.

The part determination unit 12 reads collation patterns corresponding to the examination parts to be continuously examined from the collation pattern memory 15 according to the determination order decided by the determination order decision unit 13 and sequentially collates the B-mode image signal generated by the image generation unit 3 in this determination order, using the read collation patterns, to determine the imaging part of the subject.

The imaging condition setting unit 11 stores imaging conditions corresponding to a plurality of examination parts in advance and sets the imaging conditions corresponding to the examination part determined by the part determination unit 12.

The apparatus control unit 14 controls the imaging condition setting unit 11, the display control unit 4, the part determination unit 12, and the determination order decision unit 13 on the basis of commands input from by the information input unit 16 by the user.

The storage unit 17 stores, for example, an operation program. For example, a recording medium, such as a hard disk, a flexible disk, a magneto-optical disk (MO), a magnetic tape (MT), a random access memory (RAM), a compact disk read only memory (CD-ROM), a digital versatile disk read only memory (DVD-ROM), a secure digital card (SD card), a compact flash card (CF card), or a universal serial bus memory (USB memory), or a server may be used as the storage unit 17.

In this embodiment, the image generation unit 3, the display control unit 4, the transmission/reception control unit 8 of the transmitting/receiving unit 2, the imaging condition setting unit 11, the part determination unit 12, the determination order decision unit 13, and the apparatus control unit 14 are formed by a central processing unit (CPU) and an operation program that causes the CPU to perform various processes. However, these units may be formed by digital circuits. In addition, some or all of the image generation unit 3, the display control unit 4, the transmission/reception control unit 8, the imaging condition setting unit 11, the part determination unit 12, the determination order decision unit 13, and the apparatus control unit 14 may be integrated into one CPU.

Figure 4:
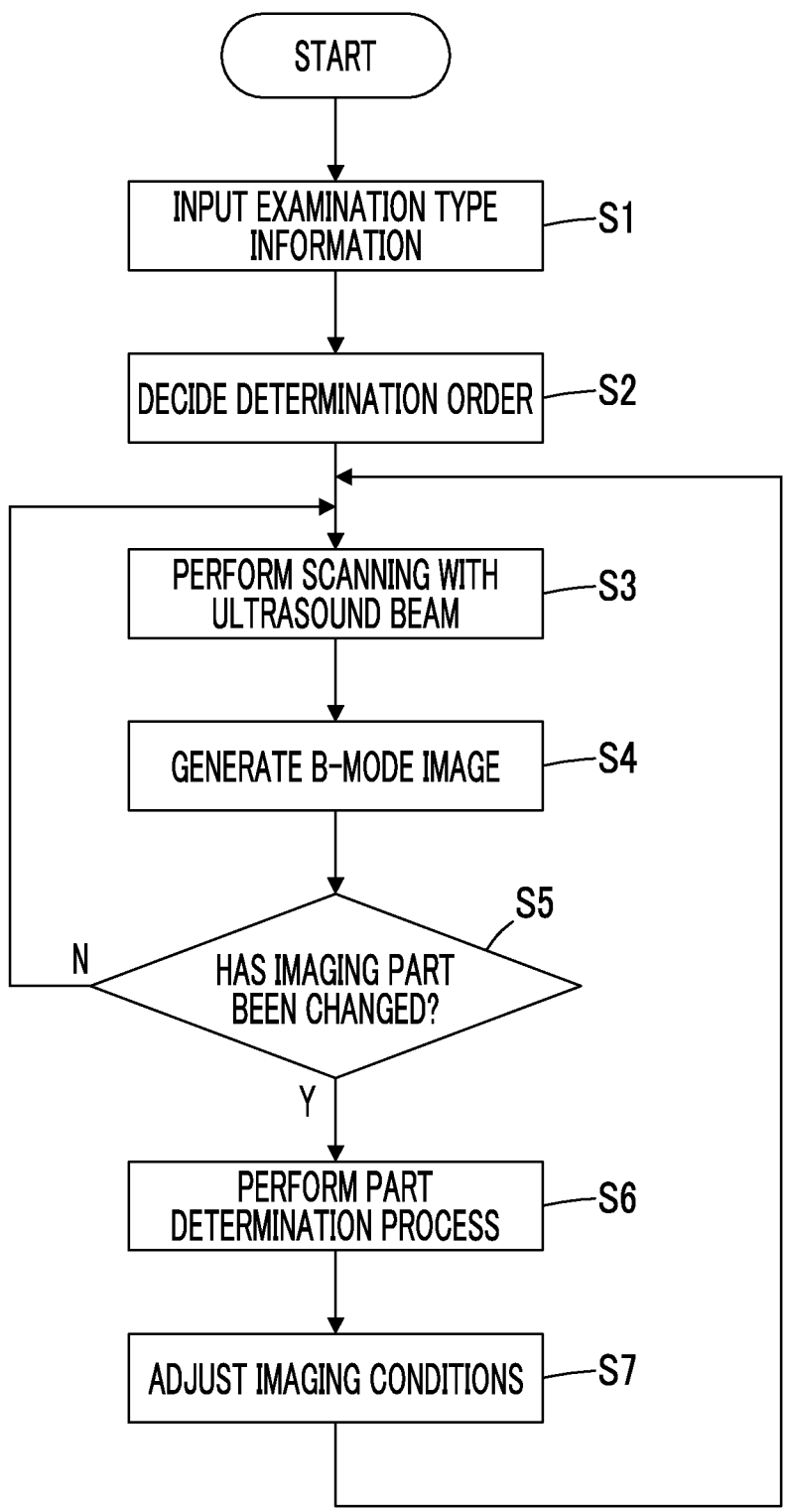
FIG. 4 is a flowchart illustrating the operation of Embodiment 1.

Next, the operation of Embodiment 1 will be described with reference to a flowchart illustrated in FIG. 4.

First, in Step S1, the user inputs examination type information to the information input unit 16. The examination type information indicates the content of an examination that continuously examines a plurality of examination parts in a case in which the subject is diagnosed. For example, in a continuous examination that is generally called an eFAST examination, the right abdomen, the left abdomen, a region around the bladder, an epigastric region, the right lung, and the left lung are continuously examined in this order. In addition, examples of the continuous examination include an abdomen routine examination that continuously examines the liver, the gallbladder, the kidney, the pancreas, and the spleen in this order and a circulatory organ routine examination that continuously examines the long and short axes of the left ventricle, the cardiac apex, the right heart, and an epigastric region in this order. The content and order of the examination parts are illustrative and vary depending on, for example, examination facilities, examiners, and the state of a patient.

Here, in a case in which the user selects the eFAST examination from the continuous examination candidates, the eFAST examination is input as the examination type information to the information input unit 16.

Then, in Step S2, the determination order decision unit 13 decides the determination order of a plurality of examination parts to be continuously examined on the basis of the examination type information. The determination order decision unit 13 stores the content of a plurality of continuous examinations in advance and decides a plurality of examination parts to be continuously examined, such as the right abdomen, the left abdomen, the region around the bladder, the epigastric region, the right lung, and the left lung, on the basis of the examination type information such as the eFAST examination input by the user. In addition, the determination order decision unit 13 decides the determination order for determining imaging parts in the order of the right abdomen, the left abdomen, the region around the bladder, the epigastric region, the right lung, and the left lung and outputs the decided determination order to the part determination unit 12.

In Step S3, the transmitting/receiving unit 2 performs the transmission and reception of an ultrasound beam and scanning, using the plurality of ultrasound transducers in the array transducer 1A of the ultrasound probe 1. A received signal from each ultrasound transducer that has received ultrasound echoes from the subject is output to the receiving unit 7. The receiving unit 7 performs amplification and A/D conversion for the received signal to generate received data.

In Step S4, the received data is input to the image generation unit 3. The B-mode processing unit 9 performs the reception focusing process for the received data and the DSC 10 converts received data to generate a B-mode image signal. The B-mode image signal is output from the image generation unit 3 to the display control unit 4. The B-mode image is displayed on the display unit 5.

The B-mode image signal output from the DSC 10 of the image generation unit 3 is input to the part determination unit 12. First, in Step S5, the part determination unit 12 determines whether the imaging part in the B-mode image signal has been changed. For example, in a case in which the examination part is changed from the right abdomen to the left abdomen and the imaging part is changed, it is determined that the imaging part has been changed. Specifically, in general, in a case in which the imaging part is changed, the probe is separated from the surface of the body and emits ultrasonic waves to the air. Therefore, it is possible to determine whether the imaging part has been changed by detecting the aerial emission state (a state in which a reflected signal is not obtained). Alternatively, in a case in which the B-mode image signal is generated first after the determination order is decided in Step S2, the process proceeds to Step S6 in order to determine the imaging part and to set the imaging conditions corresponding to the determination result. Then, in Step S6, the part determination unit 12 determines the imaging part of the subject.

First, the part determination unit 12 reads the collation patterns corresponding to the examination parts of the eFAST examination from the collation pattern memory 15 according to the determination order decided by the determination order decision unit 13. The collation pattern memory 15 stores collation patterns corresponding to the stomach, the kidney, the liver, and various other imaging parts in order to respond to examination parts other than the examination parts of the eFAST examination. Only six types of collation patterns corresponding to the right abdomen, the left abdomen, the region around the bladder, the epigastric region, the right lung, and the left lung which are the examination parts of the eFAST examination are read from the collation pattern memory 15 storing the various other collation patterns.

In addition, the part determination unit 12 sequentially collates the B-mode image signal output from the DSC 10 of the image generation unit 3 in the determination order decided by the determination order decision unit 13 using the read collation patterns. That is, as illustrated in the flowchart of FIG. 5, the B-mode image signal is collated in the order of the right abdomen, the left abdomen, the region around the bladder, the epigastric region, the right lung, and the left lung using the collation patterns corresponding to these examination parts.

For example, in the examination of the right lung, in a case in which it is determined in Step S11 that the imaging part is not the right abdomen, it is determined in Step S12 that the imaging part is not the left abdomen, it is determined in Step S13 that the imaging part is not the region around the bladder, it is determined in Step S14 that the imaging part is not the epigastric region, and it is determined in Step S15 that the imaging part is the right lung, Step S16 is omitted. In Step S18, it is confirmed that the imaging part is the right lung and the determination result is output. Then, the part determination process ends.

As such, only six collation patterns corresponding to the examination parts of the eFAST examination are read and collation is performed in Steps S11 to S16. Therefore, even in a case in which collation patterns other than six types of collation patterns corresponding to the examination parts of the eFAST examination are stored in the collation pattern memory 15, it is possible to prevent the time required for the part determination process from increasing.

Figure 5:
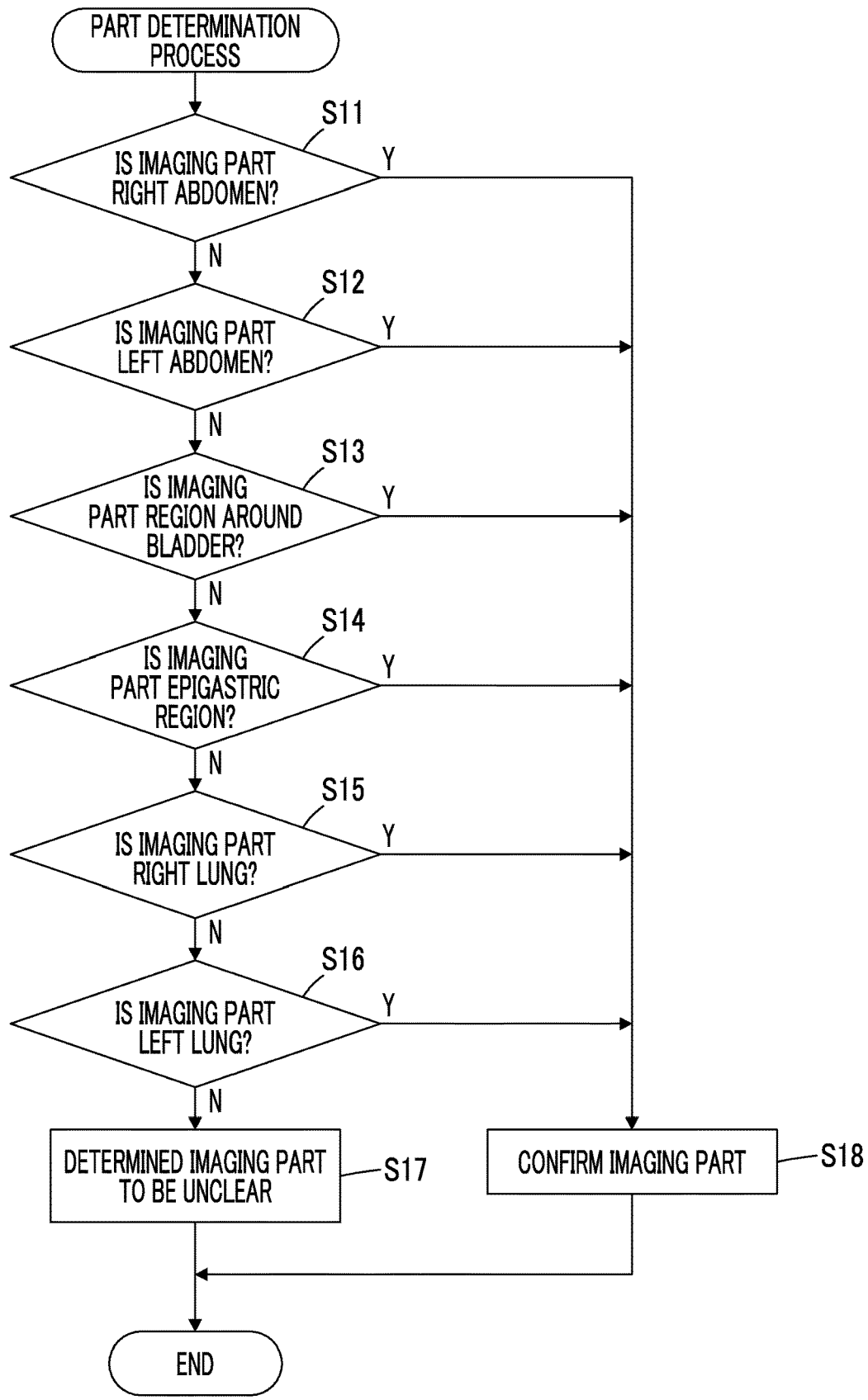
FIG. 5 is a flowchart illustrating a part determination process according to Embodiment 1.

In a case in which the imaging part is the liver that is not the examination part of the eFAST examination, in the flowchart illustrated in FIG. 5, Steps S11 to S16 are performed using only the read six types of collation patterns and it is determined in Step S17 that the imaging part is unclear. Therefore, it is possible to prevent the time until the process proceeds to an operation subsequent to the part determination process from increasing.

In a case in which the eFAST examination starts to examine the right abdomen which is an initial examination part and it is determined in Step S11 that the imaging part is the right abdomen, Steps S12 to S16 are not performed and it is confirmed in Step S18 that the imaging part is the right abdomen. Then, the part determination process is completed. Therefore, the collation of the B-mode image signal in Step S12 and the subsequent steps is omitted and it is possible to reduce the time required for the part determination process.

A known matching technique can be used to collate the B-mode image signal using the read collation patterns. In addition to the matching technique, for example, machine learning or a general image recognition method may be used to calculate similarity and the B-mode image signals may be collated on the basis of the calculated similarity.

In a case in which the part determination unit 12 outputs, for example, the determination result indicating that the imaging part is the right abdomen, the imaging condition setting unit 11 adjusts the imaging conditions in Step S7. The imaging condition setting unit 11 stores a plurality of imaging conditions in advance, selects imaging conditions corresponding to the output determination result, and controls the transmitting/receiving unit 2 and the image generation unit 3 such that imaging is performed for the subsequent frames under the selected imaging conditions.

Then, returning to Step S3, the transmission/reception control unit 8 of the transmitting/receiving unit 2 is controlled such that an ultrasound beam is transmitted and received according to ultrasound beam scanning conditions included in the imaging conditions selected by the imaging condition setting unit 11. Then, in Step S4, the image generation unit 3 is controlled such that a B-mode image is generated from the received signal according to ultrasound image generation conditions included in the imaging conditions selected by the imaging condition setting unit 11. The B-mode image signal is output from the image generation unit 3 to the display control unit 4. In this way, the B-mode image suitable for diagnosing the right abdomen can be displayed on the display unit 5.

Then, Steps S3 to S5 are repeated until the part determination unit 12 determines that the imaging part has been changed in Step S5 and the right abdomen which is the imaging part is continuously diagnosed.

Then, for example, in a case in which the examination part is changed from the right abdomen to the left abdomen, the part determination unit 12 determines that the imaging part has been changed in Step S5. Then, in Step S6, the part determination unit 12 determines that the imaging part is the left abdomen. In Step S7, the imaging condition setting unit 11 selects the imaging conditions corresponding to the determination result and the transmitting/receiving unit 2 and the image generation unit 3 are controlled such that a B-mode image signal suitable for diagnosing the left abdomen which is the imaging part is generated.

In the imaging conditions, the ultrasound beam scanning conditions can include, for example, an ultrasound beam transmission frequency, a focal position, and a display depth and the ultrasound image generation conditions can include, for example, a sound speed, detection conditions, a gain, a dynamic range, a gradation curve, speckle reduction strength, and end enhancement.

As described above, the content of a plurality of continuous examinations is stored in the determination order decision unit 13 in advance. However, the user may operate the information input unit 16 to edit the stored content of the examinations and to store the edited content of the examinations in the determination order decision unit 13. For example, assuming that the abdomen routine examination which continuously examines the liver, the gallbladder, the kidney, the pancreas, and the spleen in this order is stored in the determination order decision unit 13, the user can change one of a plurality of examination parts from the liver to the stomach and edit the content of the examination such that the stomach, the gallbladder, the kidney, the pancreas, and the spleen are examined in this order. In addition, the examination order may be changed without changing the examination part.

As described above, in the part determination process for the imaging part in the B-mode image signal, a plurality of collation patterns which have been read according to the determination order are used one by one and the imaging part is confirmed at the time when the imaging part in the B-mode image signal is determined to the examination part corresponding to the collation pattern used for collation. However, the invention is not limited thereto. For example, for the imaging part in the B-mode image signal, similarities to the collation patterns corresponding to the right abdomen, the left abdomen, the region around the bladder, the epigastric region, the right lung, and the left lung may be calculated and the examination part corresponding to a collation pattern with the highest similarity may be confirmed as the imaging part.

In a case in which the similarity is calculated as described above, only six types of collation patterns corresponding to the examination parts, such as the right abdomen, the left abdomen, the region around the bladder, the epigastric region, the right lung, and the left lung decided by the determination order decision unit 13, are used. Therefore, it is possible to prevent the time required for the part determination process from increasing.

Embodiment 2

In Embodiment 1, the part determination unit 12 reads the collation patterns from the collation pattern memory 15 according to the determination order decided by the determination order decision unit 13 and determines the imaging part in the B-mode image signal using only the read collation patterns. However, the invention is not limited thereto. In Embodiment 2, a collation pattern corresponding to an examination part which is located in the vicinity of the examination part corresponding to the collation pattern read by the part determination unit 12 is stored in the collation pattern memory 15 in advance. Then, the collation pattern corresponding to the examination part which is located in the vicinity of the examination part corresponding to the read collation pattern is read from the collation pattern memory 15 so as to be added to the collation patterns read by the part determination unit 12. Then, the imaging part can be determined.

In a case in which the user inputs the eFAST examination as the examination type information to the information input unit 16, first, the determination order decision unit 13 decides a plurality of examination parts to be continuously examined such as the right abdomen, the left abdomen, a region around the bladder, an epigastric region, the right lung, and the left lung. In addition, the determination order decision unit 13 decides a determination order for determining an imaging part in the order of the right abdomen, the left abdomen, the region around the bladder, the epigastric region, the right lung, and the left lung and outputs the decided determination order to the part determination unit 12. The part determination unit 12 reads collation patterns corresponding to the right abdomen, the left abdomen, the region around the bladder, the epigastric region, the right lung, and the left lung from the collation pattern memory 15 according to the decided determination order.

Here, the collation patterns corresponding to examination parts which are located in the vicinity of the examination part of the eFAST examination, for example, the cardiac apex and a parasternal region which are located in the vicinity of the epigastric region are also stored in the collation pattern memory 15 in advance. In addition, the examination parts which are located in the vicinity of the examination part of the eFAST examination are stored in the part determination unit 12 in advance. The collation patterns corresponding to the cardiac apex and the parasternal region which are located in the vicinity of the epigastric region are also read from the collation pattern memory 15.

As illustrated in the flowchart of FIG. 6, the collation patterns corresponding to the examination parts, such as the right abdomen, the left abdomen, the region around the bladder, the epigastric region, the right lung, the left lung, the cardiac apex, and the parasternal region, are used in this order and the B-mode image signal output from the DSC 10 of the image generation unit 3 is collated.

For example, in a case in which the parasternal region located in the vicinity of the epigastric region is examined, it is impossible to determine the imaging parts in Steps S11 to S16 corresponding to the right abdomen, the left abdomen, the region around the bladder, the epigastric region, the right lung, and the left lung which are the content of the eFAST examination. It is determined in Step S21 that the imaging part is not the cardiac apex. Then, it is determined in Step S22 that the imaging part is the parasternal region. It is confirmed in Step S18 that the imaging part is the parasternal region.

As such, for example, in the eFAST examination, in a case in which the examination part that is anomalously located in the vicinity of the epigastric region needs to be examined, the part determination unit 12 can read the collation patterns corresponding to the parasternal region and the cardiac apex located in the vicinity of the epigastric region to determine the imaging part.

The part determination unit 12 may read the collation pattern corresponding to the examination part of the eFAST examination and the collation patterns corresponding to the examination parts located in the vicinity of the examination part of the eFAST examination at the time when the determination order decided by the determination order decision unit 13 is input. In addition, in the flowchart illustrated in FIG. 5 in Embodiment 1, at the time when the imaging part is determined not to be the left lung in Step S16, the part determination unit 12 may read the collation patterns corresponding to the examination parts located in the vicinity of the examination part of the eFAST examination and may collate the B-mode image signal using the read collation patterns.

Embodiment 3

In Embodiment 1 and Embodiment 2, the examination type information is selected from a plurality of continuous examination candidates by the user and is then input to the information input unit 16. However, in Embodiment 3, the examination type information is input as a list of a plurality of examination parts selected by the user to the information input unit 16.

The user selects, for example, the liver, the gallbladder, the kidney, the pancreas, and the spleen from various examination part candidates and inputs a list of examination type information indicating the content of the examination that continuously examines the examination parts to the information input unit 16. Then, the determination order decision unit 13 decides the determination order of the liver, the gallbladder, the kidney, the pancreas, and the spleen on the basis of the input examination type information and outputs the determination order to the part determination unit 12. The part determination unit 12 performs the part determination process which reads the collation patterns corresponding to the examination parts from the collation pattern memory 15 according to the determination order decided by the determination order decision unit 13, collates the B-mode image signal output from the DSC 10 of the image generation unit 3 in the order of the liver, the gallbladder, the kidney, the pancreas, and the spleen, using the collation patterns corresponding to the examination parts, and determines the imaging part.

As such, the user can arbitrarily select a plurality of examination parts and input a list of examination type information.

EXPLANATION OF REFERENCES

1: ultrasound probe
1A: array transducer
2: transmitting/receiving unit
3: image generation unit
4: display control unit
5: display unit
6: transmitting unit
7: receiving unit
8: transmission/reception control unit
9: B-mode processing unit
10: DSC
11: imaging condition setting unit
12: part determination unit
13: determination order decision unit
14: apparatus control unit
15: collation pattern memory
16: information input unit
17: storage unit
18: amplification unit
19: A/D conversion unit
20: beam former
21: signal processing unit

What is claimed is:

1. An ultrasound diagnostic apparatus comprising:
an ultrasound probe;
a collation pattern memory that stores a plurality of collation patterns corresponding to a plurality of examination parts of a subject in advance;
an information input device that is used by a user to input examination type information indicating content of an examination for continuously examining the plurality of examination parts; and
a processor configured
to transmit and receive an ultrasound beam to and from the subject using the ultrasound probe and convert a received signal output from the ultrasound probe into an image to generate an ultrasound image of the subject;
to decide a determination order of the plurality of examination parts to be continuously examined, on the basis of the examination type information input through the information input device; and
to read the collation patterns corresponding to the examination parts to be continuously examined from the collation pattern memory according to the determination order decided and sequentially collate the ultrasound image generated in the determination order using the read collation patterns to determine an imaging part of the subject,
wherein the processor reads, from the collation pattern memory, a collation pattern corresponding to an examination part which is located in the vicinity of the examination part corresponding to the read collation pattern from the collation pattern memory, in addition to the collation patterns read from the collation pattern memory according to the determination order, and determines the imaging part.

2. The ultrasound diagnostic apparatus according to claim 1,
wherein the processor stores content of a plurality of continuous examinations for continuously examining the plurality of examination parts in advance, and
in a case in which the user inputs a continuous examination selected from the plurality of continuous examinations as the examination type information through the information input device, the processor decides the determination order of the plurality of examination parts corresponding to the input continuous examination.

3. The ultrasound diagnostic apparatus according to claim 1,
wherein the examination type information is input as a list of the plurality of examination parts to be continuously examined through the information input device by the user, and
the processor decides the determination order of the plurality of examination parts on the basis of the list input through the information input device.

4. The ultrasound diagnostic apparatus according to claim 1,
wherein the processor sets imaging conditions corresponding to the imaging part determined and,
generates the ultrasound image according to the imaging conditions.

5. The ultrasound diagnostic apparatus according to claim 2,
wherein the processor sets imaging conditions corresponding to the imaging part determined and generates the ultrasound image according to the imaging conditions.

6. The ultrasound diagnostic apparatus according to claim 3,
wherein the processor sets imaging conditions corresponding to the imaging part determined and generates the ultrasound image according to the imaging conditions.

7. A method for controlling an ultrasound diagnostic apparatus, the method comprising:

a step of transmitting and receiving an ultrasound beam to and from a subject using an ultrasound probe and converting a received signal output from the ultrasound probe into an image to generate an ultrasound image of the subject;

a step of allowing a user to input examination type information indicating content of an examination for continuously examining a plurality of examination parts;

a step of deciding a determination order of the plurality of examination parts to be continuously examined, on the basis of the input examination type information; and a step of reading collation patterns corresponding to the examination parts to be continuously examined from a plurality of collation patterns, which correspond to the plurality of examination parts and are stored in advance, according to the decided determination order and sequentially collating the ultrasound image in the determination order using the read collation patterns to determine an imaging part of the subject, wherein, in the step of reading collation patterns, a collation pattern corresponding to an examination part which is located in the vicinity of the examination part corresponding to the read collation pattern from a collation pattern memory, is read from the collation pattern memory, in addition to the collation patterns read from the collation pattern memory according to the determination order.

* * * * *